United States Patent [19]

Takami et al.

[11] Patent Number: 4,958,514
[45] Date of Patent: Sep. 25, 1990

[54] GAS SENSING ELEMENT

[75] Inventors: Akio Takami; Toshitaka Matsuura; Keizo Furusaki, all of Aichi, Japan

[73] Assignee: NGK Spark Plug Co., Ltd., Aichi, Japan

[21] Appl. No.: 273,621

[22] Filed: Nov. 17, 1988

Related U.S. Application Data

[63] Continuation of Ser. No. 83,018, Aug. 3, 1987, abandoned, which is a continuation of Ser. No. 786,576, Oct. 4, 1985, abandoned.

[30] Foreign Application Priority Data

Oct. 13, 1984 [JP] Japan .................. 59-215044

[51] Int. Cl.$^5$ .......................................... G01N 27/04
[52] U.S. Cl. ..................................... 73/25.03; 338/34; 422/98
[58] Field of Search .................... 73/27 R, 23, 25, 26; 338/34; 422/98; 204/424, 431

[56] References Cited

U.S. PATENT DOCUMENTS

| | | | |
|---|---|---|---|
| 4,001,756 | 1/1977 | Heijne | 422/98 |
| 4,066,413 | 1/1978 | Segawa et al. | 422/98 |
| 4,377,801 | 3/1983 | Weber et al. | 338/34 |
| 4,414,531 | 11/1983 | Novak | 422/98 |
| 4,443,781 | 4/1984 | Ohta et al. | 338/34 |
| 4,481,499 | 11/1984 | Arima et al. | 338/34 |
| 4,505,803 | 3/1985 | Mare et al. | 422/98 |
| 4,509,034 | 4/1985 | Sakai | 422/98 |
| 4,532,492 | 7/1985 | Esper et al. | 338/34 |

FOREIGN PATENT DOCUMENTS

| 5194595 | 1/1976 | Japan | 338/34 |
|---|---|---|---|
| 0009996 | 1/1979 | Japan | 422/98 |

Primary Examiner—John F. Niebling
Assistant Examiner—Ben C. Hsing
Attorney, Agent, or Firm—Sughrue, Mion, Zinn, Macpeak & Seas

[57] ABSTRACT

A gas sensing element, such as may be used to sense the presence of oxygen contained in the exhaust from a burner or internal combustion engine, whereby, by preventing the re-sintering of functional layers of the sensing element, a deterioration of the performance of the element under high-temperature operating conditions is prevented. The inventive sensing element includes a ceramic susbtrate, an electrode layer formed on the ceramic substrate, a first functional layer overlying the ceramic susbtrate and the electrode layer and which contains a transition metal oxide as a main component, and a second functional layer that cover the first functional layer and which contains 1 to 30 wt % of an anti-sintering agent and has a transition metal oxide as a main component.

3 Claims, 3 Drawing Sheets

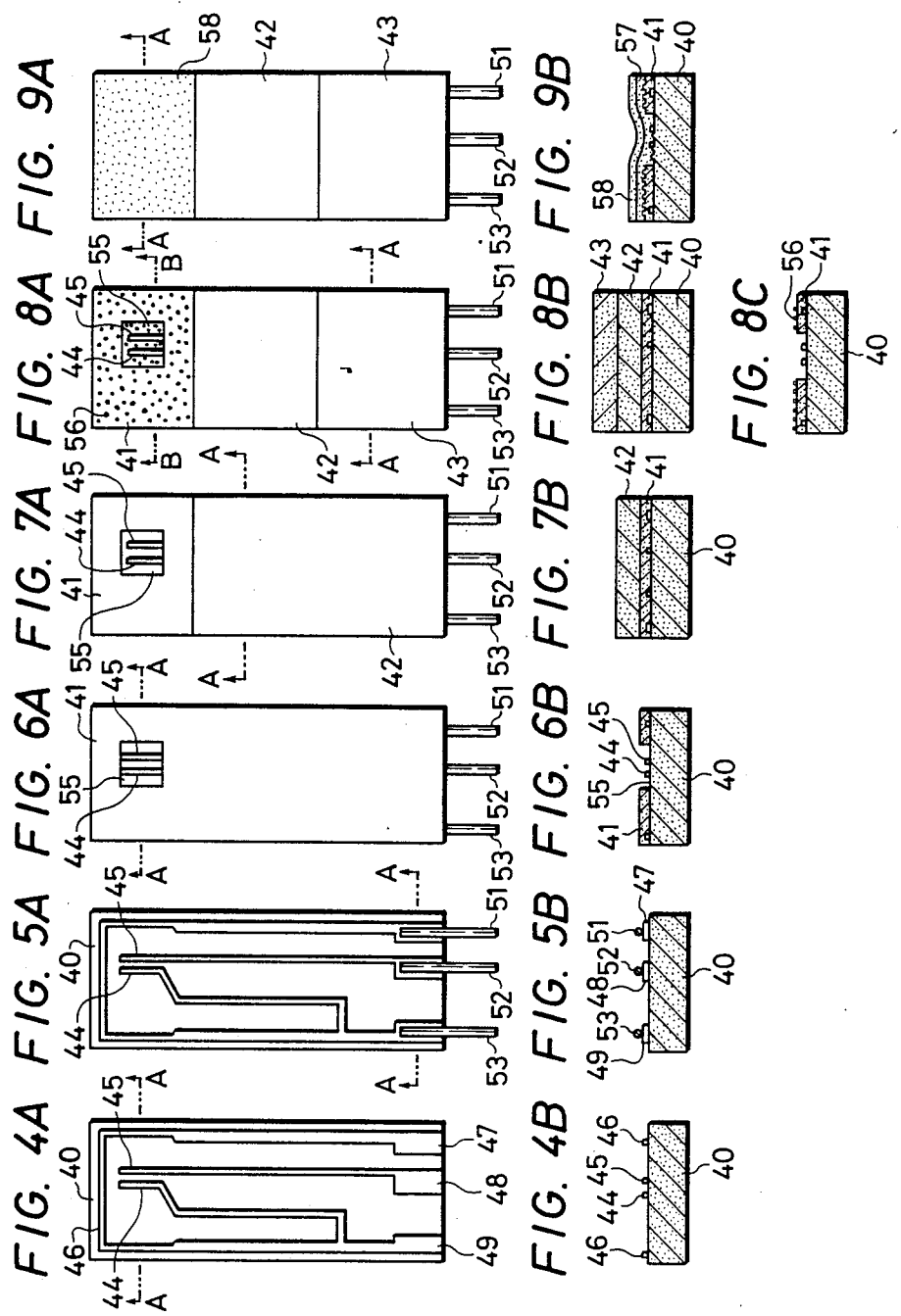

GAS SENSING ELEMENT

This is a continuation of Ser. No. 083,018, filed Aug. 13, 1987, which is a continuation of Ser. No. 786,576, filed Oct. 11, 1985, both now abandoned.

BACKGROUND OF THE INVENTION

The present invention relates to a gas sensing element for detecting the presence of a predetermined gas in the ambient atmosphere using a transition metal oxide whose resistance is dependent on the presence of that gas and its concentration.

Several types of gas sensing elements have conventionally been used to detect the presence of a predetermined gas in the ambient atmosphere or measure its concentration. Generally, these elements use as a functional (active) layer $TiO_2$, ZnO, $SnO_3$ or other transition metal oxides that undergo a change in their electrical resistance upon contact with the certain gas. In order to meet the requirements for a simpler construction and higher productivity, it has been proposed that such gas sensing elements be produced employing a hybrid technique, whereby an electrode layer is formed on a substrate made of a ceramic insulator and a functional layer containing one or more of the above-described transition metal oxides as the main component is formed on the electrode layer.

For achieving a higher gas sensitivity, the porosity of the functional layer in these gas sensing elements is desirably maintained in the range of 25 to 50%, and in order to attain this range of porosity, the functional layer is usually sintered at temperatures in a range of about 900 to 1200° C.

When a gas sensing element produced by the method described above is used to detect a predetermined gas in a hot exhaust flow from an internal combustion engine or other burner, the sensing element itself is exposed to the hot gas, which inevitably causes the resintering of the functional layer. When this occurs, the porosity of the functional layer changes to such an extent that the performance of the sensing element is deteriorated.

Proposals have been made to prevent the resintering of the functional layer by the addition of $Na_2O$, $Cr_2O_3$, $Al_2O_3$ or $ZrO_2$ (see, for example, Japanese Unexamined Published Pat. application No. 57143/1980). However, these anti-sintering agents react with the transition metal oxide and cause an undesired change in the sensor's performance, such as an increased bulk resistivity.

SUMMARY OF THE INVENTION

The present invention has been accomplished in order to solve this problem, and a principal object of the invention is to provide a gas sensing element that enables reliable detection of a predetermined gas component in a hot exhaust, or the concentration of that gas component, inducing any change in the sensor's performance, even if it is exposed to the high-temperature environment of the exhaust gas.

The above stated object of the invention is achieved by a gas sensing element comprising a ceramic substrate, an electrode layer formed on said ceramic substrate, a first functional layer that overlies said ceramic substrate and said electrode layer and which contains a transition metal oxide as its main component, and a second functional layer that overlies said first functional layer and which contains 1 to 30 wt% of an anti-sintering agent and has a transition metal oxide as its main component.

The ceramic substrate used in the device of the present invention may be any conventional ceramic substrate, such as one prepared by firing a composition that contains alumina, beryllia, mullite or steatite as its principal component.

The electrode layer may be made of any electrical conductor that is capable of withstanding the high temperature used in firing the ceramic substrate. Preferably, the electrode layer is formed of a conductive material that contains gold or a platinum group metal as its main component. Platinum is especially preferred since it has an electrical resistance and thus can be directly used as a circuit element.

The type of the transition metal oxide used in the first and second functional layers is determined by the gas component to be detected. Illustrative transition metal oxides that may be used in the invention include $TiO_2$, ZnO, $SnO_2$, $Nb_2O_5$ and $CeO_2$, and it is preferred for the purposes of the invention to use one or more of these materials. When these materials are used in the functional layers, elemental platinum or a mixture of platinum and rhodium is preferably added as a catalyst in order to provide a device having an improved gas sensitivity. The addition of such catalysts may be accomplished by blending them with the transition metal oxide in the form of either a powder or solution, and then thermally decomposing the blend. The catalyst is preferably incorporated in an amount not smaller than 1 mol% but not greater than 20 mol% of the transition metal oxide. If the content of the catalyst is less than 1 mol% of the transition metal oxide, it is insufficient for achieving the state of equilibrium with the unburnt gas in the exhaust. If more than 20 mol% of the catalyst is used, the catalyst particles contact one another and cause electrical shorting in the device, thereby degrading its performance. The second functional layer does not make direct contact with the electrode layer, and any electrical shorting between individual catalyst particles will not lead to an appreciably degraded device performance. Therefore, this second layer permits the addition of the catalyst in an amount slightly higher than 20 mol% of the transition metal oxide.

Any of the known anti-sintering agents may be incorporated in the second functional layer, which include $Cr_2O_3$, $Al_2O_3$, $SiO_2$ and $ZrO_2$. The present inventors have found that the re-sintering of the device occurs principally in its surface area that is exposed to the hot gas, while the inside of the device remains fairly stable. On the basis of this finding, the amount of the anti-sintering agent incorporated in the first functional layer which makes direct contact with the electrode is limited to no more than 1%, and the greater part of that layer should be composed of a transition metal oxide so that the bulk resistivity of the layer is held low. On the other hand, an amount of anti-sintering agent should be incorporated in the second functional layer sufficient to prevent any re-sintering of the device, thereby maintaining its gas sensing ability at an optimal level. If the second functional layer has an increased bulk resistivity, the entire device will have a slightly increased bulk resistivity and its mechanical strength will be reduced. It is therefore desired that the second functional layer have both a reduced bulk resistivity and a suitable strength. In consideration of these requirements, the amount of the anti-sintering agent incorporated in the second functional layer is desirably not less than 1 wt% of that layer for the purpose of ensuring its ability to prevent re-sintering. On the other hand, the amount of the anti-sintering agent is desirably not more than 30 wt% of the second functional layer in order to maintain its bulk resistivity at a low level and to obtain the desired mechanical strength. For the purpose of minimizing the bulk resistivity of the second functional layer, it is desired that $ZrO_2$ containing no less than 5 mol% of $Y_2O_3$ be used as the anti-sintering agent. In this case, better results are obtained if the $Y_2O_3$ content is in the range of about 5 to 13 mol%. The function of $Y_2O_3$ in $ZrO_2$ is threefold: stabilizing $ZrO_2$, increasing its electrical conductivity, and reducing the bulk resistivity of the second functional layer. It is difficult to stabilize $ZrO_2$ without adding at least 5 mol% of $Y_2O_3$, and hence the $ZrO_2$ used as the anti-sintering agent preferably contains no less than 5 mol% of $Y_2O_3$.

The thickness of each of the first and second functional layers should be properly determined depending upon the specific use of the sensing element. Desirably, each layers has a thickness between 50 microns and 200 microns, with the combined thickness of the two layers being in the range of 100 to 300 microns. If each functional layer has a thickness of less than 50 microns, it will be subjected to the direct effects of the exhaust, and a layer that is sufficiently thin and which yet is uniform in thickness is difficult to form. A functional layer thicker than 300 microns is also undesirable since it has a reduced response due to slow gas exchange in the device. Furthermore, such a thick layer is highly likely to separate from the ceramic substrate during service. In order to avoid this problem, it is desired that the bonding strength between the first functional layer and the ceramic substrate be increased by texturizing that part of the surface of the substrate which is to be overlaid with the first functional layer. Conventionally, functional layers overlying the ceramic substrate, as in the case of the sensing element of the present invention, are sometimes protected by forming an outer insulator coat by a suitable technique such as the thermal spraying of spinel. Such an insulator coat may also be formed on the second functional layer in the sensing element of the present invention.

BRIEF DESCRIPTION OF THE DRAWINGS

FIGS. 4A to 9B illustrate a sequence of steps for assembling a gas sensing element, wherein the "A" figures are front views, the "B" figures cross sections taken along lines A—A, and FIG. 8C is a cross section taken on a line B—B; and FIGS. 10A and 10B show how a set of Pt lead wires are connected to a set of terminals, wherein FIG. 10A is a front view of the gas sensing element and FIG. 10B is a side view of the element as seen from the right side.

DESCRIPTION OF THE PREFERRED EMBODIMENTS

An embodiment wherein a sensing element of the invention is used as an oxygen sensor for detecting the concentration of oxygen in the exhaust from an internal combustion engine or other burner will hereunder be described with reference to the accompanying drawings. The sensing element according to this embodiment has not only an electrode layer and two functional layers on the ceramic substrate, but also a heater layer that heats the functional layers to provide an enhanced gas sensing ability.

Figure 1:
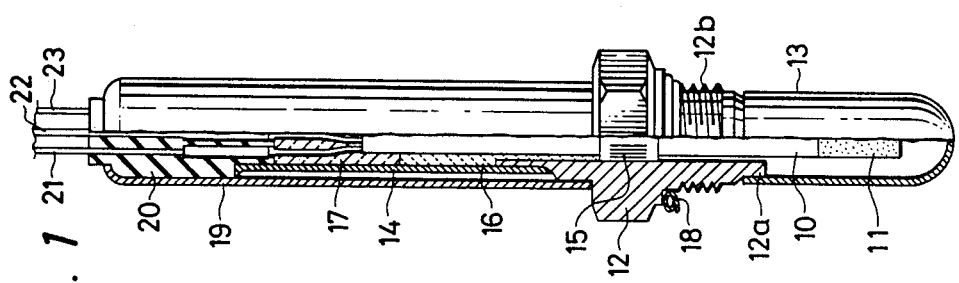
FIG. 1 is a fragmentary sectional view showing the general construction of a sensor of the invention.

FIG. 1 is a fragmentary sectional view of the oxygen sensor according to one embodiment of the invention. In this Figure, reference numeral 10 denotes a gas sensing element having at the end 11 a functional layer for detecting the oxygen concentration in the exhaust gas; 12 is a tubular metal retainer that holds the gas sensing element 10 and which facilitates the mounting of the sensor on an exhaust pipe a burner; 13 is a protector that protects the sensing element 10 and which is mounted on the end 12a of the metal retainer 12 which is connected to the burner; 14 is an inner sleeve that holds the sensing element 10 together with the metal retainer 12. The gas sensing element 10 is held by the retainer 12 and the inner sleeve 14 with an intervening spacer 15, filler powder 16 and glass seal 17. The outer periphery of the metal retainer 12 is provided with a male thread 12b by which the retainer is mounted on the exhaust pipe or burner. That part of the metal retainer 12 which is to contact the wall of the exhaust pipe or burner is made gas-tight by being provided with a gasket 18.

The filler powder 16 is made of a 1:1 mixture of talc and glass powders and is used to fix the gas sensing element 10 within the inner sleeve 14. The glass seal 17 is made of a low-melting glass and has two functions: preventing leakage of the gas to be detected, and protecting the terminals on the gas sensing element 10.

Figure 3:
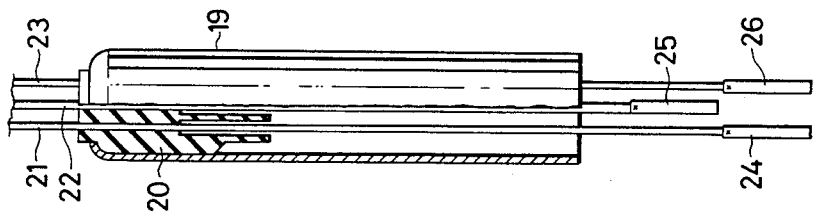
FIG. 3 is a fragmentary sectional view showing the interior of an outer sleeve of the sensor of FIG. 1.
Figure 2:
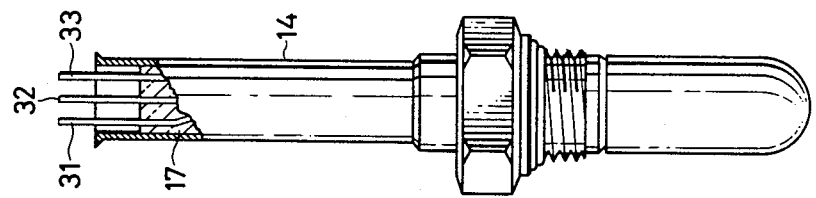
FIG. 2 is a fragmentary sectional view showing an inner sleeve and terminals projecting beyond a glass seal of the sensor of FIG. 1.

An outer sleeve 19 is mounted on the metal retainer 12 so as to cover the inner sleeve 14. A sealant 20 made of silicone rubber is provided for insulating and protecting the junctions between a set of lead wires 21 to 23 and a set of terminals 31 to 33 on the gas sensing element 10 that project from the glass seal 17 as shown in FIG. 2. The set of lead wires 21 to 23 may be connected to the set of terminals 31 to 33 by first, as shown in FIG. 3 placing the sealant 20 and the lead wires 21 to 23 within the outer sleeve 19, connecting tabs 24 to 26 to the set of lead wires 21 to 23 at their end, and subsequently connecting the tabs 24 to 26 to the terminals 31 to 33 by clamping.

The gas sensing element 10 used in the illustrated embodiment is fabricated by the procedures shown in FIGS. 4A to 9B. FIGS. 4A, 5A, 6A, 7A, 8A and 9A are each a front view, and FIGS. 4B, 5B, 6B, 7B, 8b and 9B are respective cross sections of the former taken on a line A—A. FIG. 8C is a cross section of FIG. 8A taken on a line B—B. FIGS. 4A to 9B are intended as illustrations of a sequence of steps used for the fabrication of the gas sensing element 10. For purposes of clarity, the dimensions of each of the components of the element are not in agreement with those used in FIG. 1, as is also true with the device shown in FIGS. 10A and 10B.

Referring to FIGS. 4A to 9B, each of reference numerals 40 to 43 denotes a green sheet that is prepared as follows: 100 parts by weight of a powder mixture (average particle size: 1.5 microns) consisting of $Al_2O_3$ (92 wt%), $SiO_2$ (4 wt%), CaO (2 wt%), and MgO (2 wt%), is blended with 12 parts by weight of a butyral resin and 6 parts by weight of dibutyl phthalate (DBP). The respective components are mixed in an organic solvent to form a slurry, which is then processed into a sheet by a doctor blade. The green sheet 40 has a thickness of 1 mm, and the green sheet 41 a thickness of 0.2 mm, while each of the green sheets 42 and 43 has a thickness of 0.8 mm.

Each of reference numerals 44 to 49 denotes a pattern printed as a thick film from a platinum paste containing 7 wt% of $Al_2O_3$; 44 and 45 are electrode patterns each corresponding to the electrode layer defined above that provides an electrode for the functional layers; 46 is a resistive heating pattern that provides a heater for heating the functional layers; 47 to 49 are electrode patterns for either supplying a voltage to the heating pattern 46 and the functional layers or conducting a detected signal therefrom.

The process of fabricating the gas sensing element 10 starts with printing patterns 44 to 49 on the green sheet 40 in the form of thick films of platinum paste, as shown in FIGS. 4A and 4B. Then, as shown in FIG. 5, Pt lead wires 51 to 53, each having a diameter of 0.2 mm, are respectively provided on the electrode patterns 47 to 49.

Following this step, as is clear from FIGS. 6A and 6B, an opening 55 is formed in the green sheet 41 by blanking out the area that corresponds to the tips of the electrode patterns 44 and 45. The green sheet 41 is then placed on the green sheet 40 so as to cover all patterns 44 to 49 except for the tips of the electrode patterns 44 and 45. The two sheets are next thermally compressed together.

Subsequently, as shown in FIGS. 7A and 7B, the green sheet 42 is placed on the green sheet 41 of the resulting assembly and the two sheets are bonded together by thermal compression. Then, as shown in FIGS. 8A and 8B, the green sheet 43 is placed on part of the green sheet 42 to form a step, and the two sheets are joined together by thermal compression. A powder of ceramic particles 56 is then coated onto the green sheet 41 so as to cover the bottom of the opening 55 and the entire surface of that green sheet (FIG. 8C). The ceramic powder has a particle size of 80 to 150 mesh and is prepared by spray drying an aqueous solution in 4 wt% of polyvinyl alcohol (PVA) of a powder having the same composition as that used for forming the green sheets 40 to 43. The layer of ceramic coat is pressed at 50° C. under 8 kg/cm² so as to provide a textured surface for that part of the green sheet 41 where the functional layers are to be formed.

By the above procedures, an assembly having a stepped arrangement of the green sheets 41 to 43 is provided, wherein the Pt lead wires 51 to 53 partly project and the tips of the electrode patterns 44 and 45 are left uncovered. This assembly is then left in a heated atmosphere (1,500° C.) for 2 hours to form a fired ceramic substrate.

The ceramic substrate having electrode layers formed as above is then overlaid with a first functional layer 57 and a second functional layer 58, as shown in FIGS. 9A and 9B. This step completes the fabrication of the gas sensing element 10.

The following description, which is closely related to the Experiment to be discussed below, assumes the fabrication of a plurality of gas sensing elements 10, wherein the first functional layer 57 and the second functional layer 58 contain anti-sintering agents of different compositions in different amounts.

The process of overlying the two functional layers 57 and 58 on the ceramic substrate proceeds as follows.

First, to a $TiO_2$ powder (average particle size: 1.2 microns) is added as anti-sintering agent (for its composition and amount, see the Table below). Then, platinum black is added in an amount of 10 mol% of $TiO_2$ Ethyl cellulose is also added in an amount of 3 wt% of the total powder. The respective components are mixed in a solvent, or Butyl Carbitol (tradename for 2-(2-butoxyethoxy)ethanol), to prepare a $TiO_2$ paste having a viscosity of 300 poise. Each of the pastes thus prepared is then applied in the opening 55 and over the green sheet 41 in a predetermined amount so as to attain one of the thicknesses indicated in the Table which follows. The applied paste is dried by heating at 100° C. for 15 minutes to form the first functional layer 57. The same method may be employed to form the second functional layer 58 on the first functional layer 57. The ceramic substrate thus overlaid with the first and second functional layers 57 and 58 is heated to 800° C. in the atmosphere, fired in $N_2$ gas at 1,200° C. for 2 hours, and then furnace-cooled to obtain the desired gas sensing element 10.

Figures 10A, 10B:
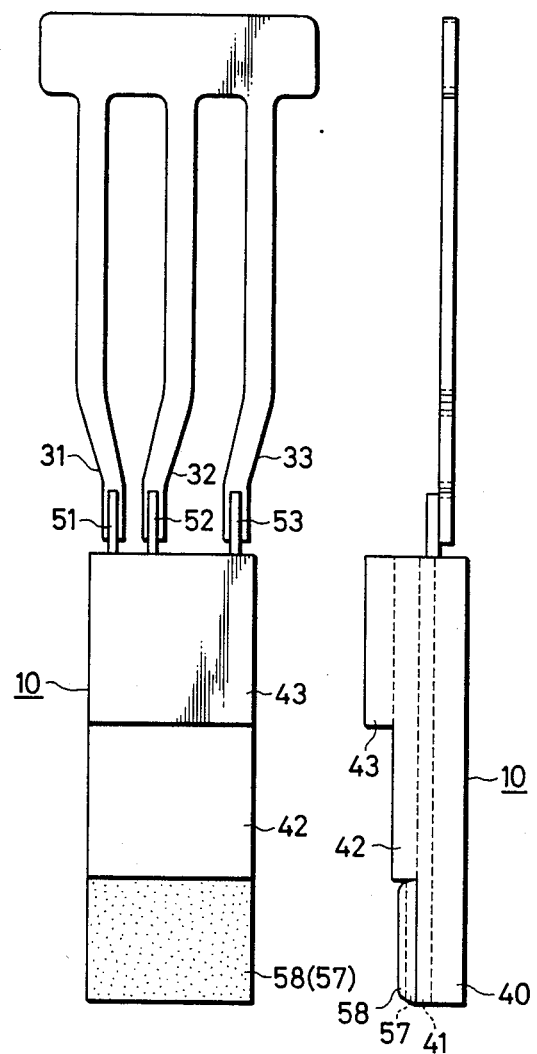

The process of connecting a set of terminals 31 to 33 to the set of Pt lead wires 51 to 53 that project outwardly from the sensing element 10 is illustrated in FIGS. 10A and 10B. The set of terminals 31 to 33 are integral parts of a 0.3 mm thick nickel plate that are formed by an etching technique. These terminals are welded to respective ones of the Pt lead wires 51 to 53. The gas sensing element 10 is then inserted into the metal holder 12, and after placing the glass seal 17 around part of the substrate as well as the junction between the set of terminals 31 to 33 and the set of Pt lead wires 51 to 53, the element 10 is fixed within the inner tube 14. Subsequently, a predetermined length of the set of terminals 31 to 33 is cut off the nickel plate. FIG. 10A is a front view of the gas sensing element 10 and FIG. 10B is a side view of the element as seen from the right side.

EXPERIMENT

A plurality of gas sensing elements 10 were prepared using the procedures described above, except that the functional layers had different compositions. These sensing elements were employed as oxygen sensors, and their bulk resistivities and response characteristics were determined. The determination of the response characteristics was made in terms of the response time of each sensor, which was connected to the exhaust system of a propane gas burner. The response time was taken as the time required for sensor's output to change from 66% to 33% of the theoretical maximum as a result of a change in excess air ratio from 0.9 to 1.1. The initial values of the bulk resistivity and response time of each sensor were obtained by performing tests with a propane gas burner for an exhaust gas temperature of 350° C. immediately after the fabrication of that sensor. Thereafter, the sensor was exposed to another propane gas burner (exhaust temperature: 950° C., air excess ratio: 0.9) for 50 hours. After this exposure, another run of the measurements of the bulk resistivity and response time was conducted using a propane gas exhaust at 350° C. The functional layers of each sensing element were heated by applying a voltage of 12 volts to the resistive heater pattern 46. The results of these tests were shown in the following Table.

TABLE

| O$_2$ Sensor No. | First functional layer | | | Second functional layer | | | Initial | | After 50-hour exposure to exhaust | | Remarks |
| --- | --- | --- | --- | --- | --- | --- | --- | --- | --- | --- | --- |
| | Type of sintering agent | Amount of addition (wt %) | Thickness ($\mu$m) | Type of sintering agent | Amount of addition (wt %) | Thickness ($\mu$m) | Bulk resistivity (K$\Omega$) | Response time (msec) | Bulk resistivity (K$\Omega$) | Response time (msec) | |
| 1 | None | 0 | 200 | none | | | 1.5 | 40 | 1.5 | 120 | Outside the scope of the invention |
| 2 | Al$_2$O$_2$ | 5 | 200 | none | | | 2.1 | 48 | 9.5 | 35 | Outside the scope of the invention |
| 3 | ZrO$_2$ | 5 | 200 | none | | | 2.8 | 35 | 10.1 | 32 | Outside the scope of the invention |
| 4 | None | 0 | 100 | Al$_2$O$_2$ | 5 | 100 | 1.8 | 62 | 3.2 | 47 | Within the scope of the invention |
| 5 | None | 0 | 100 | ZrO$_2$ | 5 | 100 | 2.0 | 50 | 4.8 | 45 | Within the scope of the invention |
| 6 | None | 0 | 100 | ZrO$_2$/ 8 mol Y$_2$O$_3$ | 5 | 100 | 1.6 | 52 | 1.8 | 50 | Within the scope of the invention |
| 7 | None | 0 | 100 | ZrO$_2$/ 8 mol Y$_2$O$_3$ | 1 | 100 | 1.5 | 63 | 1.5 | 85 | Within the scope of the invention |
| 8 | None | 0 | 100 | ZrO$_2$/ 8 mol Y$_2$O$_3$ | 15 | 100 | 2.5 | 60 | 2.9 | 55 | Within the scope of the invention |
| 9 | None | 0 | 100 | ZrO$_2$/ 8 mol Y$_2$O$_3$ | 30 | 100 | 3.5 | 45 | 4.7 | 53 | Within the scope of the invention |
| 10 | None | 0 | 50 | ZrO$_2$/ 8 mol Y$_2$O$_3$ | 5 | 100 | 2.2 | 35 | 2.8 | 42 | Within the scope of the invention |
| 11 | None | 0 | 100 | ZrO$_2$/ 8 mol Y$_2$O$_3$ | 5 | 50 | 1.8 | 38 | 2.5 | 65 | Within the scope of the invention |
| 12 | None | 0 | 100 | ZrO$_2$/ 8 mol Y$_2$O$_3$ | 0.5 | 100 | 1.5 | 48 | 1.7 | 110 | Outside the scope of the invention |
| 13 | None | 0 | 100 | ZrO$_2$/ 8 mol Y$_2$O$_3$ | 35 | 100 | 4.2 | 39 | 4.8 | 42 | Outside the scope of the invention |
| 14 | ZrO$_2$/ 8 mol Y$_2$O$_3$ | 0.2 | 100 | ZrO$_2$/ 8 mol Y$_2$O$_3$ | 5 | 100 | 1.6 | 53 | 1.7 | 72 | Within the scope of the invention |

The amount of anti-sintering agents added to the first and second functional layers are the weight proportions of such agents relative to TiO$_2$, which constituted the major portion of each functional layer. The notation "ZrO$_2$/8 mole Y$_2$O$_3$" in the column headed "Type of anti-sintering agent" for the first and second functional layers means that the anti-sintering agent used is ZrO$_2$ containing 8 mol% of Y$_2$O$_3$.

Referring to the Table, Sensor No. 1 used a gas sensing element having only one functional layer and with no anti-sintering agent. After a 50-hour exposure to the exhaust from the propane gas burner, this sensor experienced no change at all in bulk resistivity, indicating that the absence of an anti-sintering agent is preferred for the purpose of holding the bulk resistivity of a gas sensor at a low level. However, the data for this sensor also shows that, because of the absence of an anti-sintering agent, the device was re-sintered as a result of exposure to the exhaust gas, and its response time was much increased, making the device no longer usable as a gas sensor. Sensors Nos. 2 and 3 had only one functional layer but employed an anti-sintering agent. In this case, the response time was not increased, but the bulk resistivity of each device was so high as to make it unsuitable for use as a gas sensor.

Sensors Nos. 4 to 13 were prepared by incorporating an anti-sintering agent only in the second functional layer. All of these sensors, except Nos. 12 and 13, performed satisfactorily. Sensor No. 12 contained only 0.5 mol% of anti-sintering agent and the functional layers were re-sintered, causing an increase in their response times. The amount of anti-sintering agent incorporated in the second functional layer must be at least 1 wt%, as in the case of Sensor No. 7. On the other hand, for Sensor No. 13 which contained as much as 35 wt% of anti-sintering agent in the second functional layer, not only was its bulk resistivity high in the initial state, but also the second functional layer had been sintered insufficiently and would separate from the first functional layer upon receiving the slightest impact. Sensor No. 7 experienced a relatively great increase in response time, but no change occurred in its bulk resistivity. Therefore, it is concluded that in order to ensure a minimum increase in bulk resistivity, the amount of anti-sintering agent is preferably low, not only in the first functional layer, but also in the second functional layer. Sensor No. 14 contained 0.2 wt% of an anti-sintering agent in the first functional layer in addition to 5 mol% of the same anti-sintering agent in the second functional layer. The data for this sensor shows that the first functional layer may also contain an anti-sintering agent so long as the amount thereof does not exceed 1 wt%.

Sensors Nos. 4 to 6 contained different types of anti-sintering agent in the second functional layer. The data for these sensors shows that the lowest bulk resistivity can be obtained by using an anti-sintering agent composed of ZrO$_2$ containing 8 mol% of Y$_2$O$_3$.

As described herein, the gas sensing element of the present invention includes as basic elements a ceramic support, an electrode layer formed on the support, a first functional layer that overlies the substrate and electrode layer and which contains a transition metal oxide as its main component, and a second functional layer that overlies the first functional layer and which contains 1 to 30 wt% of an anti-sintering agent and has a transition metal oxide as its main component. Even if this gas sensing element is used with a burner where the functional layers are exposed to a hot gas, the anti-sintering agent in the second functional layer prevents its re-sintering, and at the time, the first functional layer, which is protected by the second functional layer, is also prevented from being re-sintered. Since the first functional layer is prevented from re-sintering even if it does not contain any anti-sintering agent, the combined bulk resistivity of the functional layers is not significantly increased by the addition of the anti-sintering agent. In short, in accordance with the present invention, a gas sensing element exhibiting good and stable sensing characteristics is provided, and any re-sinstering of the functional layers that could lead to deteriorated sensing characteristics is prevented without causing an increase in bulk resistivity.

We claim:

1. A gas sensing element comprising: a ceramic substrate having the heater incorporated therein, an electrode layer formed on said ceramic substrate which provides an electrode disposed on the surface of the ceramic substrates; a first functional layer having a high gas sensitivity that overlies said ceramic substrate and said electrode layer and cover said electrode and which contains a transition metal oxide of one or more members selected from the group consisting of $TiO_2$, AnO, $SnO_2$, $Nb_2O_5$, and $CeO_2$ as a main component; and a second functional layer that has a high durability and that overlies said first functional layer and which contains 1 to 30 wt% of $ZrO_2$ containing no less than 5 mol% of $Y_2O_3$ as an anti-sintering agent and has a transition metal oxide of one or more members selected from the group consisting of $TiO_2$, ZnO, $SnO_2$, $Nb_2O_5$, and $CeO_2$ as a main component, such that said gas sensing element is capable of operation at a temperature of 350° C. and deterioration of the sensing characteristics of the functional layers due to re-sintering is prevented without causing an increase in bulk resistivity.

2. The gas sensing element according to claim 1, wherein a side of said ceramic substrate joins with said first functional layer has a textured surface.

3. The gas sensing element according to claim 1, wherein each of said functional layers has a thickness between 50 microns and 200 microns, with the combined thickness of said two functional layers being in the range of 100 to 300 microns.

* * * * *